(12) United States Patent
Xu et al.

(10) Patent No.: US 8,030,097 B2
(45) Date of Patent: Oct. 4, 2011

(54) LIPOCALIN-2 AS A PROGNOSTIC AND DIAGNOSTIC MARKER FOR HEART AND STROKE RISKS

(75) Inventors: Aimin Xu, Upper Baguio Villa (HK); Yu Wang, Upper Baguio Villa (HK); Reinhard Renneberg, Clear water Bay (HK); George William Hunter Cautherley, Mountain Lodge (HK); Cangel Pui Yee Chan, Yuen Long (HK); Matthias Lehmann, Berlin (DE)

(73) Assignee: Versitech Limited and R & C Biogenius Limited, Hong Kong (CN)

( * ) Notice: Subject to any disclaimer, the term of this patent is extended or adjusted under 35 U.S.C. 154(b) by 0 days.

(21) Appl. No.: 12/113,056

(22) Filed: Apr. 30, 2008

(65) Prior Publication Data
US 2009/0274709 A1    Nov. 5, 2009

(51) Int. Cl.
*G01N 33/53* (2006.01)
(52) U.S. Cl. .................... 436/811; 435/7.1; 436/501
(58) Field of Classification Search ............ None
See application file for complete search history.

(56) References Cited

U.S. PATENT DOCUMENTS

2005/0244892 A1* 11/2005 Lazar et al. ............ 435/7.1
2008/0254485 A1* 10/2008 Valkirs et al. ............ 435/7.4

OTHER PUBLICATIONS

Miller et al., Use of BNP and CRP as Biomarkers in Assessing Cardiovascular Disease: Diagnosis Versus Risk, Current Vascular Pharmacology, 2007, 5, pp. 15-25.*
Choi et al., Implication of lipocalin-2 and visfatin levels in patients with coronary heart disease, European Journal of Endocrinology, Feb. 1, 2008, 158, pp. 203-207.*
Hraba-Renevy, Suzanne and Kress, Michel. 1989. Expression of a mouse replacement histone H3.3 gene with a highly conserved 3' noncoding region during SV40- and polyoma-induced Go to S-phase transition. *Nucleic Acids Research*. 17(7):2449-2461.
Kjeldsen et al. 1993. Isolation and Primary Structure of NGAL, a Novel Protein Associated with Human Neutrophil Gelatinase. *J Biol Chem*. 268(14):10425-10432.
Akerstrom et al. 2000. Lipocalins: unity in diversity. *Biochimica et Biophysica Acta*. 1482:1-8.
Flower, Darren R. 1996. The lipocalin protein family: structure and function. *Biochem J*. 318:1-14.
Bratt et al. 1999. Interactions between neutrophil gelatinase-associated lipocalin and natural lipophilic ligands. *Biochimica et Biophysica Acta*. 1472:262-269.
Liu, Quansheng and Nilsen-Hamilton, Marit. 1995. Identification of a New Acute Phase Protein. *J Biol Chem*. 270(38):22565-22570.
Kratchmarova et al. 2002. A Proteomic Approach for Identification of Secreted Proteins during the Differentiation of 3T3-L1 Preadipocytes to Adipocytes. *Molecular & Cellular Proteomics*. 1:213-222.
Meheus et al. 1993. Identification by Microsequencing of Lipopolysaccharide-Induced Proteins Secreted by Mouse Macrophages. *J Immunol*. 151:1535-1547.
Jayaraman et al. 2005. Identification of Neutrophil Gelatinase-Associated Lipocalin (NGAL) as a Discriminatory Marker of the Hepatocyte-Secreted Protein Response to IL-1β: a Proteomic Analysis. *Biotechnol Bioeng*. 91:502-515.
Mishra et al. 2005. Neutrophil gelatinase-associated lipocalin (NGAL) as a biomarker for acute renal injury after cardiac surgery. *Lancet*. 365:1231-1238.
Mishra et al. 2003. Identification of Neutrophil Gelatinase-Associated Lipocalin as a Novel Early Urinary Biomarker for Ischemic Renal Injury. *Journal of the American Society of Nephrology*. 14:2534-43.
Mishra et al. 2004. Neutrophil Gelatinase-Associated Lipocalin: A Novel Early Urinary Biomarker for Cisplatin Nephrotoxicity. *American Journal of Nephrology*. 24:307-15.
Reghunathan et al. 2005. Expression profile of immune response genes in patients with Severe Acute Respiratory Syndrome. *BMC Immunology*. 6:2, 1-11.
Hemdahl et al. 2006. Expression of Neutrophil Gelatinase-Associated Lipocalin in Atherosclerosis and Myocardial Infarction. *Arteriosclerosis, Thrombosis & Vascular Biology*. 26(1):136-42.
Tschesche et al. 2001. The human neutrophil lipocalin supports the allosteric activation of matrix metalloproteinases. *European Journal of Biochemistry*. 268(7):1918-28.
Xu et al. 2005. Angiopoietin-like protein 4 decreases blood glucose and improves glucose tolerance but induces hyperlipidemia and hepatic steatosis in mice. *Proc Natl Acad Sci U S A* 102(17):6086-6091.
Fujino et al. 2006. Spermatogonial Cell-mediated Activation of an IκBζ-Independent Nuclear Factor-κB Pathway in Sertoli Cells Induces Transcription of the Lipocalin-2 Gene. *Mol Endocrinol* 20(4):904-915.
Hraba-Renevey, S. et al. 1989. SV40-induced expression of mouse gene 24p3 involves a post-transcriptional mechanism. *Oncogene*. 4:601-608.

\* cited by examiner

*Primary Examiner* — Melanie J Yu
*Assistant Examiner* — Gary Counts
(74) *Attorney, Agent, or Firm* — Saliwanchik, Lloyd & Eisenschenk

(57) ABSTRACT

Methods and apparatus are disclosed for the measurement of lipocalin-2 in body fluids (including but not limited to blood, serum, plasma, urine, saliva, tear, etc.) by an assay such as an immunoassay or an immunotest for (1) the prediction of risk of future cardiovascular diseases; and (2) the determination of the likelihood that certain individuals will benefit to a greater or lesser extent from the use of certain treatments designed to prevent and/or treat cardiovascular diseases.

16 Claims, 2 Drawing Sheets

LIPOCALIN-2 AS A PROGNOSTIC AND DIAGNOSTIC MARKER FOR HEART AND STROKE RISKS

BACKGROUND OF THE INVENTION

1. Field of the Invention

The present invention relates to the use of lipocalin-2 as a diagnostic marker for heart risk, chronic heart disease and stroke risk. Specifically, the present invention relates to the evaluation of risk and progression of these risks by measuring the concentration of circulating lipocalin-2 in a subject and comparing the measured level to lipocalin-2 levels within a standardized or standard population.

2. Background

Cardiovascular disease remains the most common cause of morbidity and mortality in the developed world. Therefore, prevention of cardiovascular disease is an area of major public health importance. Currently, several risk factors for future cardiovascular disease have been described and are in wide clinical use in the detection of individuals at high risk, such as evaluations of total and HDL cholesterol levels. However, a large number of cardiovascular diseases occur in individuals with apparently low to moderate risk profiles, and the ability to identify such patients is limited. Moreover, accumulating data suggests that the beneficial effects of certain preventive and therapeutic treatments for patients at risk for or known to have cardiovascular disease differ in magnitude among different patient groups. At this time, however, data describing diagnostic tests to determine whether certain therapies can be expected to be more or less effective are lacking.

Lipocalin-2, also known as 24p3 (1) and neutrophil gelatinase-associated lipocalin (NGAL) (2), is a 25 kDa secretory glycoprotein that was originally identified in mouse kidney cells and human neutrophil granules. It belongs to the lipocalin superfamily that consists of over 20 small secretory proteins, including RBP4, fatty acid binding proteins (FABP), major urinary proteins (MUP), apolipoprotein D (apoD) and prostaglandin D synthases (PGDS) (3). The common feature of this protein family is their capacity to bind and transport small lipophilic substances, such as free fatty acids, retinoids, arachidonic acid, and various steroids (4). Although it has previously been reported that lipocalin-2 binds weakly with leukotriene $B_4$ and lipopolysaccharides (5), its high affinity endogenous ligands remain to be identified. In addition to neutrophils, lipocalin-2 is expressed in several other tissues, including liver, lung, kidney, adipocytes, and macrophages (6-8). Several inflammatory stimuli, such as lipopolysaccharides and "IL-1β", can markedly induce lipocalin-2 expression and secretion in these cells (6, 9). Notably, the proinflammatory transcription factor NF-kappaB has been shown to transactivate lipocalin-2 expression through binding with a consensus motif within the promoter region of the lipocalin-2 gene (10), suggesting that this secretory protein might be involved in the inflammatory responses.

Elevated plasma lipocalin-2 levels was recently found associated with increased proteolytic activity in atherosclerotic lesions and implicated as renal failure following ischemic injury, cisplatin nephrotoxicity, or infection (11-15). The partial association of lipocalin-2 with matrix metallopeptidase 9 suggests that lipocalin-2 may exert modulatory actions on MMP9 by protecting MMP9 from degradation (2, 16), and preserving its enzymatic activity. A recent study demonstrated MMP9 and lipocalin-2 co-localized in macrophages and smooth muscle cells (SMC) in human atherosclerotic plaques. In situ zymphography showed higher MMP9 activity where lipocalin-2 are more expressed, indicating the potential role of lipocalin-2 in modulating MMP9 activity and destabilizing plaque (15).

BRIEF SUMMARY OF THE INVENTION

Embodiments of the present invention relate to the measurement of lipocalin-2 in body fluids (including but not limited to blood, serum, plasma, urine, saliva, tear, etc.) by an immunoassay or an immunotest for (1) the prediction of risk of future cardiovascular diseases; and (2) the determination of the likelihood that certain individuals will benefit to a greater or lesser extent from the use of certain treatments designed to prevent and/or treat cardiovascular diseases.

It has been discovered that an elevated level of lipocalin-2 is predictive of future cardiovascular diseases. For example, an elevated level of lipocalin-2 in apparently healthy persons is predictive of an increased risk of myocardial infarction. As another example, elevated level of lipocalin-2 is predictive of an increased likelihood of a future stroke.

It has been discovered also that the likelihood that certain individuals will benefit to a greater or a lesser extent from the use of certain therapeutic agents for reducing the risk of a future cardiovascular disease can be determined from the base-line level of lipocalin-2 in an individual. The invention is based in part on the surprising discovery that lipocalin-2 has a predictive value independent of other predictors of future cardiovascular diseases. In particular, lipocalin-2 predicts future adverse cardiovascular diseases independent of C-Reactive Protein (CRP) and myeloperoxidase (MPO). Therefore, lipocalin-2 may be used alone as a predictor for future adverse cardiovascular diseases or in combination with prior art predictors such as cholesterol, CRP, and MPO. Thus, the present invention does not involve simply duplicating a measurement that previously could be made using other predictors. Instead, level of lipocalin-2 is additive to prior art predictors.

As mentioned above, these discoveries have led to new diagnostic tests. According to one aspect of the invention, a method is provided for characterizing an individual's risk profile of developing a future cardiovascular disease. The method involves obtaining a level of lipocalin-2 in the individual. The level of lipocalin-2 then is compared to a predetermined value, and the individual's risk profile of developing a future cardiovascular disease then is characterized based upon the level of lipocalin-2 in comparison to the predetermined value. The predetermined value can be a single value, multiple values, a single range or multiple ranges. Thus, in one embodiment, the predetermined value is a plurality of predetermined marker level ranges, and the comparing step comprises determining in which of the predetermined marker level ranges the individual's level falls.

According to still another aspect of the invention, a method is provided in which one uses a lipocalin-2 level together with another known cardiovascular disease marker, such as a cholesterol fraction or CRP or MPO for characterizing an individual's risk profile of developing a future cardiovascular disease. A level of lipocalin-2 in the individual is obtained. The level of the lipocalin-2 is compared to a first predetermined value to establish a first risk value. A level of a cholesterol or CRP or MPO in the individual also is obtained. The level of the second marker (such as cholesterol or CRP or MPO) in the individual is compared to a second predetermined value to establish a second risk value. The individual's risk profile of developing the cardiovascular disease then is characterized based upon the combination of the first risk value and the second risk value, wherein the combination of the first risk value and second risk value establishes a third risk value different from the first and second risk values.

According to yet another aspect of the invention, a method is provided for evaluating the likelihood that an individual will benefit from treatment with an agent for reducing the risk of a cardiovascular disease. The agent can be selected from the group consisting of anti-inflammatory agents, anti-thrombotic agents, anti-platelet agents, fibrinolytic agents, lipid reducing agents, direct thrombin inhibitors, and glycoprotein IIb/IIIa receptor inhibitors and agents that bind to cellular adhesion molecules and inhibit the ability of white blood cells to attach to such molecules (e.g. anti-cellular adhesion molecule antibodies). To practice the method, a level of lipocalin-2 in an individual is obtained. This level then is compared to a predetermined value, wherein the level of lipocalin-2 in comparison to the predetermined value is indicative of the likelihood that the individual will benefit from treatment with the agent. The individual then can be characterized in terms of the net benefit likely to be obtained by treatment with the agent.

Thus, the invention provides information for evaluating the likely net benefit of certain treatments for candidate patients.

The invention also contemplates kits comprising a package including an assay for lipocalin-2 and instructions, and optionally related materials such as number or color charts, for correlating the level of lipocalin-2 as determined by the assay with a risk of developing a future cardiovascular disease or with other patient criteria as described above. In further embodiments, the kits also include an assay for at least a second marker, such as cholesterol, CRP, MPO, or other related markers.

DETAILED DESCRIPTION OF THE INVENTION

Definitions

Figure 1A:
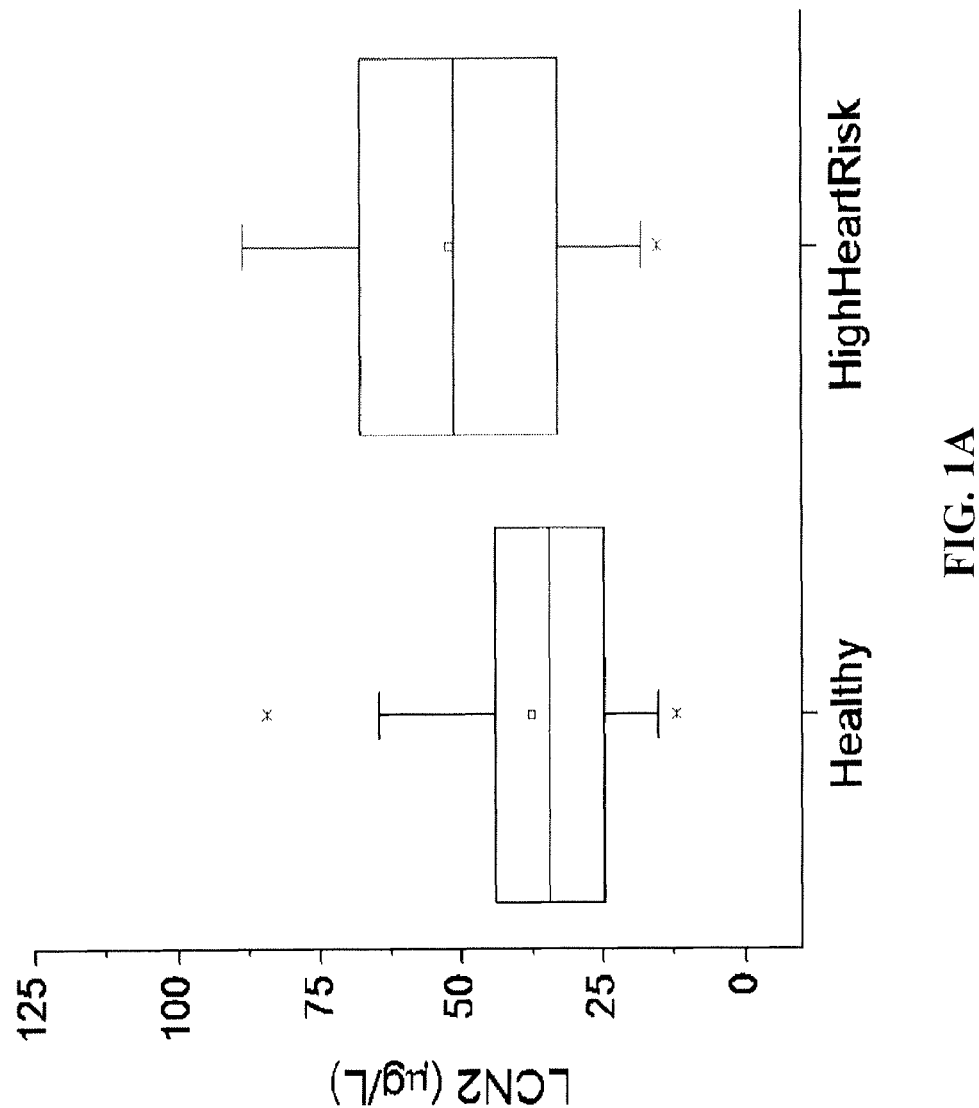
FIGS. 1A and 1B show Serum and urinary lipocalin-2 (LCN2) in patients with high-risk in heart attack/stroke. Concentrations are shown (y-axis) for patients with high-risk in heart attack/stroke (n=46), and for 36 healthy control subjects (x-axis). The lines inside the boxes denote medians whilst the boxes mark the interval between the $25^{th}$ and $75^{th}$ percentiles. The whiskers denote the interval between the $10^{th}$ and $90^{th}$ percentiles. The differences in serum and urinary LCN2 concentrations between high-risk group and healthy group (P<0.001 and P<0.05 respectively) are statistically significant.

The term "test sample" as used in this specification refers to a sample of biological fluid obtained for the purpose of diagnosis, prognosis, or evaluation of a subject of interest, such as a patient. In certain embodiments, such a sample may be obtained for the purpose of determining the outcome of an ongoing condition or the effect of a treatment regimen on a condition. Preferred test samples include, but are not limited to, blood, serum, plasma, urine, saliva, and tears. In addition, one of skill in the art would realize that some test samples would be more readily analyzed following a fractionation or purification procedure, for example, separation of whole blood into serum or plasma components.

As used herein the terms cardiovascular disease (CVD) and coronary artery disease (CAD) are interchangeable and are intended to encompass, but are not limited to, heart disease, atherosclerosis, microvascular disease, hypertension, stroke, diabetic angiopathies, myocardial infarction, acute coronary syndrome, unstable angina, and diabetic retinopathy.

The term "diagnosis" as used in this specification refers to predict the type of disease or condition from a set of risk values and/or patient symptoms. This is in contrast to disease prediction, which is to predict the occurrence of disease before it occurs, and the term "prognosis," which is to predict disease progression at a future point in time from one or more indicator value(s) at a previous point in time.

The term "marker" as used herein refers to substances such as proteins or polypeptides or other substances used as targets for screening test samples obtained from subjects. "Proteins or polypeptides" used as markers in the present invention are contemplated to include any immunologically detectable fragments, identifiable as fragments thereof. One of skill in the art would recognize that proteins which are released by cells of the central nervous system which become damaged during a cerebral attack could become degraded or cleaved into such fragments. Additionally, certain markers are synthesized in an inactive form, which may be subsequently activated, e.g., by proteolysis. Examples of such markers are include interleukin-1 beta (IL-1β), and many others are known in the art. The term "related marker" as used herein refers to one or more fragments of a particular marker that may be detected as a surrogate for the marker itself. These related markers may be, for example, "pre," "pro," or "prepro" forms of markers, or the "pre," "pro," or "prepro" fragment removed to form the mature marker. Exemplary markers that are synthesized as pre, pro, and prepro forms such as IL-1B are known in the art. In preferred embodiments, these "pre," "pro," or "prepro" forms or the removed "pre," "pro," or "prepro" fragments are used in an equivalent fashion to the mature markers in the methods described herein.

It must be noted that as used herein, and in the appended claims, the singular forms of "a," "an," and "the" include plural referents unless the context clearly dictates otherwise. Thus, for example, reference to "a lipocalin-2 binding component" includes a plurality of such binding components and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

In response to the need in the art, the present invention provides methods for evaluating the risk of a mammalian subject developing a cardiovascular disease or evaluating the progression of a cardiovascular disease by employing LCN2 as a biomarker or screening tool. The present invention provides a correlation between LCN2 levels in mammalian subjects and risk level for the development or progression of cardiovascular disease.

In one aspect, the invention provides a diagnostic method for determining the risk or progression of cardiovascular disease in a mammalian subject by employing LCN2 as a novel biomarker for such diseases. Thus, the method of this invention involves determining the risk or progression of a cardiovascular disease by measuring the level of lipocalin-2 in a biological fluid of a mammalian subject. This measured level is compared to a standard of LCN2 levels in a population. An elevated LCN2 level compared to the standard is predictive of increased risk of disease. In one embodiment, a LCN2 level greater than that of the lowest 25% of the LCN2 levels forming the population is indicative of risk of cardiovascular disease. In another embodiment, if the subject's LCN2 level is greater than that of 50% of the LCN2 levels forming the population, an intermediate risk of cardiovascular disease is diagnosed. In still another embodiment, a LCN2 level greater than that of 75% of the LCN2 levels forming the population is indicative of high risk of cardiovascular disease or progression of existing cardiovascular disease. In another embodiment, a LCN2 level greater than that of 80% of the LCN2 levels forming the population is indicative of highest risk of disease.

In another aspect, a method of this invention further involves measuring the concentration of a second biomarker of cardiovascular disease or a second inflammatory biomarker in the sample and correlating the LCN2 level with the level of the second biomarker, wherein the combination of LCN2 concentration and second biomarker concentration is predictive of cardiovascular risk.

In another aspect, a method of this invention involves repeatedly measuring circulating LCN2 over time to monitor the progression of cardiovascular disease risk.

In one embodiment of these methods, plasma or serum LCN2 levels are predictive of risk of cardiovascular disease, such as atherosclerosis in mammalian subjects that are asymptomatic for cardiovascular disease and/or are not diabetic. In a further embodiment, the method of the present invention predicts cardiovascular disease risk for mammalian subjects symptomatic for metabolic syndrome. In still a further embodiment, the method of this invention assesses the risk of cardiovascular disease for subjects with diabetes. In yet another embodiment the method of this invention may be employed to track risk of such disease over time in a subject.

In yet a further aspect, the invention provides a method for treating or retarding the progression of an inflammatory disorder or cardiovascular disease in a mammalian subject by reducing the level or effect of the subject's circulating LCN2.

In accordance with the present invention, there are provided methods and apparatus for the measurement of lipocalin-2 in biological fluids (including but not limited to blood, serum, plasma, urine, saliva, tears, etc.) by an assay such as an immunoassay or an immunotest for (1) the prediction of risk of future cardiovascular diseases; and (2) the determination of the likelihood that certain individuals will benefit to a greater or lesser extent from the use of certain treatments designed to prevent and/or treat cardiovascular diseases.

According to one embodiment, a method for characterizing an individual's risk of developing a stroke, heart attack or cardiovascular disease includes obtaining a biological fluid sample from the individual, determining the lipocalin-2 concentration in the sample, and comparing the determined lipocalin-2 concentration to a predetermined reference value which is related to that of healthy individuals. The risk of developing a stroke, heart attack or cardiovascular disease is present if the lipocalin-2 concentration in the sample is elevated in comparison to the reference value. The predetermined value can be a single value, multiple values, a single range, or multiple ranges. In an embodiment where the predetermined value is a plurality of predetermined marker level ranges, the comparing of the determined lipocalin-2 concentration to the predetermined reference value can include determining in which of the predetermined marker level ranges the individual's level of lipocalin-2 falls.

The cardiovascular disease being evaluated for risk can be chronic heart disease, acute coronary symptom or heart insufficiency.

In a further embodiment, in addition to the risk value determined through lipocalin-2 concentration, the concentrations of cholesterol fractions (including HDL, LDL, or both), C-reactive protein (CRP), myeloperoxidase (MPO), or other risk markers can be determined and compared with their corresponding predetermined reference values, which are related to healthy individuals, to establish a second risk value. The individual's risk can be characterized based on the first risk value (determined through lipcalin-2 concentration) and the second risk value. In one embodiment, the individual's risk value can be characterized based on a third risk value, which is an assessment of risk based on a combination of the first risk value and the second risk value.

A. How to Measure Various Markers

One of ordinary skill in the art know several methods and devices for the detection and analysis of the markers of the instant invention. With regard to polypeptides or proteins in patient test samples, immunoassay devices and methods are often used. Alternatively, or additionally, aptamers can be selected and used for binding of even greater specificity, as is well known in the art. These devices and methods can utilize labeled molecules in various sandwich, competitive, or non-competitive assay formats, to generate a signal that is related to the presence or amount of an analyte of interest. Additionally, certain methods and devices, such as biosensors and optical immunoassays, may be employed to determine the presence or amount of analytes without the need for a labeled molecule.

Preferably the markers are analyzed using an immunoassay, although other methods are well known to those skilled in the art (for example, the measurement of marker RNA levels). The presence or amount of a marker is generally determined using antibodies specific for each marker and detecting specific binding. Any suitable immunoassay may be utilized, for example, enzyme-linked immunoassays (ELISA), radioimmunoassay (RIAs), competitive binding assays, and the like. Specific immunological binding of the antibody to the marker can be detected directly or indirectly. Direct labels include fluorescent or luminescent tags, metals, dyes, radionuclides, and the like, attached to the antibody. Indirect labels include various enzymes well known in the art, such as alkaline phosphatase, horseradish peroxidase and the like. For an example of how this procedure is carried out on a machine, one can use the RAMP Biomedical device, called the Clinical Reader Sup.™., which uses the fluorescent tag method, though the skilled artisan will know of many different machines and manual protocols to perform the same assay. Diluted whole blood is applied to the sample well. The red blood cells are retained in the sample pad, and the separated plasma migrates along the strip. Fluorescent dyed latex particles bind to the analyte and are immobilized at the detection zone. Additional particles are immobilized at the internal control zone. The fluorescence of the detection and internal control zones are measured on the RAMP Clinical Reader Sup.™., and the ratio between these values is calculated. This ratio is used to determine the analyte concentration by interpolation from a lot-specific standard curve supplied by the manufacturer in each test kit for each assay.

The use of immobilized antibodies specific for the markers is also contemplated by the present invention and is well known by one of ordinary skill in the art. The antibodies could be immobilized onto a variety of solid supports, such as magnetic or chromatographic matrix particles, the surface of an assay place (such as microtiter wells), pieces of a solid substrate material (such as plastic, nylon, paper), and the like. An assay strip could be prepared by coating the antibody or a plurality of antibodies in an array on solid support. This strip could then be dipped into the test sample and then processed quickly through washes and detection steps to generate a measurable signal, such as a colored spot.

The analysis of a plurality of markers may be carried out separately or simultaneously with one test sample. Several markers may be combined into one test for efficient processing of a multiple of samples. In addition, one skilled in the art would recognize the value of testing multiple samples (for example, at successive time points) from the same individual. Such testing of serial samples will allow the identification of changes in marker levels over time. Increases or decreases in marker levels, as well as the absence of change in marker levels, would provide useful information about the disease status that includes, but is not limited to identifying the approximate time from onset of the event, the presence and amount of salvageable tissue, the appropriateness of drug therapies, the effectiveness of various therapies, identification of the severity of the event, identification of the disease severity, and identification of the patient's outcome, including risk of future events.

An assay consisting of a combination of the markers referenced in the instant invention may be constructed to provide relevant information related to differential diagnosis. Such a panel may be constructed using 1, 2, 3, 4, 5, 6, 7, 8, 9, 10, 15, 20, or more or individual markers, though a number lower than 4 markers is the most preferred embodiment. The analysis of a single marker or subsets of markers comprising a larger panel of markers could be carried out methods described within the instant invention to optimize clinical sensitivity or specificity in various clinical settings. The clinical sensitivity of an assay is defined as the percentage of those with the disease that the assay correctly predicts, and the specificity of an assay is defined as the percentage of those without the disease that the assay correctly predicts (Tietz Textbook of Clinical Chemistry, $2^{nd}$ edition, Carl Burtis and Edward Ashwood eds., W.B. Saunders and Company, p. 496).

The analysis of markers could be carried out in a variety of physical formats as well. For example, the use of microtiter plates or automation could be used to facilitate the processing of large numbers of test samples. Alternatively, single sample formats could be developed to facilitate immediate treatment and diagnosis in a timely fashion, for example, in ambulatory transport or emergency room settings. Particularly useful physical formats comprise surfaces having a plurality of discrete, addressable locations for the detection of a plurality of different analytes. Such formats include protein microarrays, or "protein chips" (see, e.g., Ng and Ilag, J. Cell Mol. Med. 6: 329-340 (2002)) and capillary devices.

In another embodiment, the present invention provides a kit for the analysis of markers. Such a kit preferably comprises devises and reagents for the analysis of at least one test sample and instructions for performing the assay. The kit may contain aptamers specific for a target marker. Optionally the kits may contain one or more means for using information obtained from immunoassays preformed for a marker panel to rule in or out certain diagnoses. Marker antibodies or antigens may be incorporated into immunoassay diagnostic kits depending upon which marker autoantibodies or antigens are being measured. A first container may include a composition comprising an antigen or antibody preparation. Both antibody and antigen preparations should preferably be provided in a suitable titrated form, with antigen concentrations and/or antibody titers given for easy reference in quantitative applications.

The kits may also include an immunodetection reagent or label for the detection of specific immunoreaction between the provided antigen and/or antibody, as the case may be, and the diagnostic sample. Suitable detection reagents are well known in the art as exemplified by radioactive, enzymatic or otherwise chromogenic ligands, which are typically employed in association with the antigen and/or antibody, or in association with a second antibody having specificity for first antibody. Thus, the reaction is detected or quantified by means of detecting or quantifying the label. Immunodetection reagents and processes suitable for application in connection with the novel methods of the present invention are generally well known in the art.

The reagents may also include ancillary agents such as buffering agents and protein stabilizing agents, e.g., polysaccharides and the like. The diagnostic kit may further include where necessary agents for reducing background interference in a test, agents for increasing signal, software and algorithms for combining and interpolating marker values to produce a prediction of clinical outcome of interest, apparatus for conducting a test, calibration curves and charts, standardization curves and charts, and the like.

The lipocalin-2 concentration in the samples can be measured by any method of assay, preferably by aptamer binding, or by an immunological method, preferably by an immunoassay or immunotest, and more preferably by an enzyme-linked immunosorbent assay (ELISA) or a dipstick.

The measurement of the concentration of LCN2 in the biological sample may employ any suitable LCN2 antibody or aptamer to detect the protein. Such aptamers or antibodies may be presently extant in the art or presently used commercially, or may be developed by techniques now common in the field of immunology. As used herein, the term "antibody" refers to an intact immunoglobulin having two light and two heavy chains or any fragments thereof. Thus a single isolated antibody or fragment may be a polyclonal antibody, a high affinity polyclonal antibody, a monoclonal antibody, a synthetic antibody, a recombinant antibody, a chimeric antibody, a humanized antibody, or a human antibody. The term "antibody fragment" refers to less than an intact antibody structure, including, without limitation, an isolated single antibody chain, an Fv construct, a Fab construct, a light chain variable or complementarity determining region (CDR) sequence, etc. A recombinant molecule bearing the binding portion of an anti-LCN2 antibody, e.g., carrying one or more variable chain CDR sequences that bind LCN2, may also be used in a diagnostic assay of this invention. As used herein, the term "antibody" may also refer, where appropriate, to a mixture of different antibodies or antibody fragments that bind to LCN2. Such different antibodies may bind to a different portion of LCN2 than the other antibodies in the mixture. Such differences in antibodies used in the assay may be reflected in the CDR sequences of the variable regions of the antibodies. Such differences may also be generated by the antibody backbone, for example, if the antibody itself is a non-human antibody containing a human CDR sequence, or a chimeric antibody or some other recombinant antibody fragment containing sequences from a non-human source. Antibodies or fragments useful in the method of this invention may be generated synthetically or recombinantly, using conventional techniques or may be isolated and purified from plasma or further manipulated to increase the binding affinity thereof. It should be understood that any antibody, antibody fragment, or mixture thereof that binds LCN2 or a particular sequence of LCN2 as defined above or described in International Patent Publication No. WO/0064920 may be employed in the methods of the present invention, regardless of how the antibody or mixture of antibodies was generated.

Similarly, the antibodies may be tagged or labeled with reagents capable of providing a detectable signal, depending upon the assay format. Such labels are capable, alone or in concert with other compositions or compounds, of providing a detectable signal. Where more than one antibody is employed in a diagnostic method, the labels are desirably interactive to produce a detectable signal. Most desirably, the label is detectable visually, e.g. calorimetrically. A variety of enzyme systems operate to reveal a calorimetric signal in an assay, e.g., glucose oxidase (which uses glucose as a substrate) releases peroxide as a product that in the presence of peroxidase and a hydrogen donor such as tetramethyl benzidine (TMB) produces an oxidized TMB that is seen as a blue color. Other examples include horseradish peroxidase (HRP) or alkaline phosphatase (AP), and hexokinase in conjunction with glucose-6-phosphate dehydrogenase that reacts with ATP, glucose, and NAD+ to yield, among other products, NADH that is detected as increased absorbance at 340 nm wavelength.

Other label systems that may be utilized in the methods of this invention are detectable by other means, e.g., colored latex microparticles (Bangs Laboratories, Indiana) in which a dye is embedded may be used in place of enzymes to provide a visual signal indicative of the presence of the resulting LCN2-antibody complex in applicable assays. Still other labels include fluorescent compounds, radioactive compounds or elements.

Preferably, an anti-LCN2 antibody is associated with, or conjugated to a fluorescent detectable fluorochromes, e.g., fluorescein isothiocyanate (FITC), phycoerythrin (PE), allophycocyanin (APC), coriphosphine-O (CPO) or tandem dyes, PF-cyanin-5 (PE-Cy5), and PE-Texas Red (ECD). Commonly used fluorochromes include fluorescein isothiocyanate (FITC), phycoerythrin (PE), allophycocyanin (APC), and also include the tandem dyes, PE-cyanin-5 (PC5), PE-cyanin-7 (PE-Cy7), PE-cyanin-5.5, PE-Texas Red (FCD), rhodamine, PerCP, fluorescein isothiocyanate (FITC) and Alexa dyes. Combinations of such labels, such as Texas Red and rhodamine, FITC+PE, FITC+PE-Cy5 and PE-Cy7, among others may be used depending upon assay method.

Detectable labels for attachment to antibodies useful in diagnostic assays of this invention may be easily selected from among numerous compositions known and readily available to one skilled in the art of diagnostic assays. The anti-LCN2 aptamers, antibodies, or fragments useful in this invention are not limited by the particular detectable label or label system employed. Thus, selection and/or generation of suitable anti-LCN2 antibodies and aptamers with optional labels for use in this invention is within the skill of the art, provided with this specification, the documents incorporated herein, and the conventional teachings of immunology.

Similarly the particular assay format used to measure the LCN2 in a biological sample may be selected from among a wide range of immunoassays, such as enzyme-linked immunoassays, such as those described in the examples below, sandwich immunoassays, homogeneous assays, or other assay conventional assay formats. One of skill in the art may readily select from any number of conventional immunoassay formats to perform this invention.

Other reagents for the detection of protein in biological samples, such as peptide mimetics, synthetic chemical compounds capable of detecting LCN2 may be used in other assay formats for the quantitative detection of LCN2 in biological samples, such as Western blots, flow cytometry, etc.

The measurement of LCN2, preferably in plasma or serum, serves as a biomarker for CVD risk. According to the method of this invention, to determine the risk or progression of a cardiovascular disease, the level of LCN2 in a biological fluid of a mammalian subject is measured and compared to a reference standard of LCN2 levels in a population. An elevated LCN2 level compared to said standard is predictive of increased risk of disease.

The reference standard is that established by measuring LCN2 values of a normal population sample, which is naturally composed of mammalian subjects of varying degrees of cardiovascular health, from healthy, through various increasing risks of CVD/CAD to those suffering from CVD/CAD. Thus, the standard is preferably provided by using the same assay technique as is used for measurement of the subject's LCN2 levels, to avoid any error in standardization. As demonstrated in the examples below, the relative level of risk of CVD can be determined based upon the increase of LCN2 as compared against the LCN2 levels of a population.

Thus, in one embodiment, where the subject's LCN2 level is within the lowest 25% of the LCN2 levels forming the population, the subject has a "normal" level of LCN2, or a low risk of cardiovascular disease. Thus, where the subject's LCN2 level is greater than that of the lowest 25% of the LCN2 levels of the population, this measurement is indicative of some risk of cardiovascular disease. For example, in another embodiment, where the subject's LCN2 level is within the lowest 25-50% of the LCN2 levels forming the population, the subject has a low intermediate, but increased risk of cardiovascular disease. In circumstances in which the subject's LCN2 level is greater than that of 50% of the LCN2 levels forming the population, the subject is diagnosed as having an intermediate risk of cardiovascular disease. Similarly, where the subject's LCN2 level is greater than that of 75% of the LCN2 levels forming the population, the subject has a high risk of developing cardiovascular disease or is evidencing progression of existing cardiovascular disease. Finally, where the subject's LCN2 level is greater than that of 80% the LCN2 levels of the standard population, the subject is demonstrating the highest risk of disease and/or progressive cardiovascular disease.

A method of evaluating the likelihood that an individual that to be treated with a cardiovascular agent or an agent reducing the risk of a stroke, heart attack, or cardiovascular disease will benefit from a particular treatment can include: obtaining a biological fluid sample from the individual, determining the lipocalin-2 concentration in the sample, and comparing the determined lipocalin-2 concentration to a predetermined reference value. In one embodiment, the predetermined reference value can be a value obtained from previous tests or tests prior to treatment with a particular agent. The likelihood of a benefit from the treatment is present if the lipocalin-2 concentration in the sample has decreased in comparison to the reference value. In certain embodiments, the agent can be selected from the group consisting of anti-inflammatory agents, anti-thrombotic agents, anti-platelet agents, fibrinolytic agents, lipid reducing agents, direct thrombin inhibitors, and glycoprotein IIb/IIIa receptor inhibitors and agents that bind to cellular adhesion molecules and inhibit the ability of white blood cells to attach to such molecules.

Embodiments of the present invention can use lipocalin-2 as an in vitro diagnostic marker for predicting an individual risk of developing a stroke, heart attack, or cardiovascular disease.

In certain embodiments, the cardiovascular disease being predicted can be chronic heart disease, acute coronary symptom, or heart insufficiency.

Embodiments of the present invention can use a component capable of reducing lipocalin-2 concentrations in individuals for the manufacture of a pharmaceutical agent for the prevention of stroke, heart attack, or cardiovascular disease or for the treatment of a cardiovascular disease. In one embodiment, neutralizing antibodies against lipocalin-2 or chemical compounds that suppress lipocalin-2 production or antagonize lipocalin-2 biological activities can be used.

According to an embodiment, the subject invention contemplates a method of reducing the risk of stroke, heart attack, or cardiovascular disease, or treating a cardiovascular disease, by administering to a subject in need thereof a pharmaceutical agent capable of reducing circulating lipocalin-2 concentrations in the subject.

In still a further embodiment of methods according to this invention, a risk evaluation of CVD or CAD may be performed by measuring LCN2 levels in combination with measuring one or more second or other CVD/CAD biomarker. Such second or additional biomarkers include, without limitation, coronary artery calcification, high-sensitivity C-reactive protein (CRP), myeloperoxidase (MPO), markers of inflammation, lipoproteins, homocysteine, markers of fibrinolytic and hemostatic function, such as fibrinogen, D-dimer, tPA, plasminogen activator inhibitor 1 antigen, inflammatory markers, such as TNFα, LpPLA2, BNP, IL-1β, IL-18, IL-14, IL-6, TNF-α, solTNFR1 and CD40L, among others, as well as measurements of a cholesterol fraction (either HDL, LDL, or both of them) and other traditional risk factors for CVD, such as those well known in the art. Correlation between the LCN2 level and a level indicative of CVD risk for the known second biomarker further confirms the risk or progression of CVD. Thus the measurement of LCN2 may serve to confirm indications of CVD provided by assays for known biomarkers. Alternatively the measurement of LCN2 may serve to more accurately diagnose the CVD/CAD risk than the known biomarkers, such as CRP.

In yet a further embodiment, the method of this invention can include the step of repeatedly measuring LCN2 levels over a given time period, and thereby serve to monitor the progress of patients with CVD. The method may be useful to determine the degree of success of a particular therapeutic regimen for CVD/CAD and may indicate circumstances in which a change of therapy is necessary.

B. Therapeutic Methods for Treating Cardiovascular Disease or Inflammation

As a corollary to the inventors' determination that LCN2 levels are a biomarker for CAD/CAV, the present invention further provides novel therapeutic treatments for retarding the progression of CVD/CAD and/or an inflammatory disorder. Such inflammatory disorders, include without limitation, diabetes, obesity, insulin resistance, and diseases that arise from atherosclerotic cardiovascular disease, such as stroke, kidney failure, blindness and embolism, among others. Such a method provides a therapeutic regimen comprising administering to a patient an amount of a compound such as an LCN2 neutralizing antibody or LCN2 antagonist that is sufficient to reduce circulating LCN2 or otherwise inhibit its effects. Since the CVD/CAD risk levels of LCN2 increase with increases of LCN2 in plasma or serum over the standard population, described above, this method seeks to reduce LCN2 levels to successively lower risk level values. For example, for patients in the very high risk category based on serum LCN2 levels, i.e., the values in the top 75% of the standard population, the method involves neutralizing serum LCN2 to a concentration falling within the next lowest level of the standard. However, as with cholesterol levels, it is considered desirable to reduce high LCN2 levels by any value under that of the starting high risk level of LCN2. Treatment is repeated so that LCN2 levels are progressively reduced by increments until the LCN2 level is stabilized in the lowest percentile of the standard population as possible, i.e., as low or as close to normal/low risk/first 25% of the standard population as possible for the particular patient.

Thus in one embodiment, the method of the invention is directed to treating or retarding the progress of an inflammatory disorder or a cardiovascular disorder in a mammalian subject by reducing the level or effect of the subject's circulating LCN2. Desirably, the levels are reduced by at least 10% of presenting levels. Still more desirably, the levels are reduced by at least 20% of presenting levels. Using the assay described herein, one may measure the subject's LCN2 levels by comparing the subject's level to the LCN2 levels in a standard population. Thus, it is also desirable to reduce the subject's level to a level less than those with the highest quartile of the population of said standard, i.e., a 75% cut-point. According to this method, treatment may be continued to reduce the subject's LCN2 level to a level within or less than the 50-75% quartile of the standard population. According to another embodiment of this invention, the method is employed to reduce the subject's LCN2 level to a level less than that of the top 50% of the standard population. Of course, practice of the method is most desirable, where it reduces the subject's level to a level within that of the lowest 25% of the standard population.

These methods may involve repeatedly administering the antagonist or providing the patient with a course of therapy in which the circulating LCN2 level is maintained at a desired threshold level, as described herein. In certain embodiments, a pharmaceutical composition is used that comprises an agent for the prevention of stroke, heart attack, or cardiovascular disease or for the treatment of a cardiovascular disease, said agent selected from the group consisting of an anti-inflammatory agent (including aspirin and non-aspirin anti-inflammatory agents), an anti-diabetic diabetic drug [an PPAR-gamma agonist Thiazolidinediones (such as rosiglitazone)], an anti-thrombotic agent, an anti-platelet agent, a fibrinolytic agent, a lipid reducing agent, a direct thrombin inhibitor, a glycoprotein IIb/IIIa receptor inhibitor, an agent that binds to cellular adhesion molecules and inhibits the ability of white blood cells to attach to such molecules, a calcium channel blocker, a beta-adrenergic receptor blocker, a cyclooxygenase-2 inhibitor, and an angiotensin system inhibitor; the pharmaceutical composition also comprising a component capable of reducing lipocalin-2 concentrations in individuals.

Such therapeutic methods are useful for patients having existing CVD/CAD, or for asymptomatic patients having a circulating LCN2 level of greater than normal values of circulating LCN2.

The term "LCN2 antagonist" is meant any compound that can reduce circulating LCN2 to the above noted lower risk levels upon treatment than is presented before treatment. In one embodiment, the antagonist prevents the binding of LCN2 to its naturally occurring receptor. Thus, such a compound may be a synthetic drug, an anti-LCN2 antibody or fragment thereof, or a therapeutic composition that decreases expression of LCN2. Such LCN2 antagonists useful in this therapeutic method may be known compounds available commercially or in the prior art.

According to this method, suitable amounts and formulations of the selected LCN2 antagonist for administration to a patient, preferably a human patient, to accomplish the desired reduction in circulating LCN2 may be chosen by an attending physician depending upon relative factors. For example, dosages of the LCN2-reducing compounds selected vary with the particular compositions employed (the nature of the antagonist, e.g., proteinaceous, synthetic chemical, etc.), the half-life of the compound, the identity and/or stage of the cardiovascular disease or inflammatory disease, the presenting LCN2 level of the patient, the patient's age, weight, sex, general physical condition, the route of administration, any other medications and treatment, as well as the subject's medical history. Precise dosages can be determined by the administering physician based on experience with the individual subject treated. An effective therapeutic dosage contains an amount sufficient to reduce circulating LCN2 levels, and preferably sufficient to reduce starting LCN2 levels by about 20% or more.

Similarly, the routes of administration, dosage regimen and dosage frequency depends upon the factors identified above and upon the response of the patient to the therapy, as determined by periodic evaluation of the LCN2 level.

According to another embodiment, test kit is provided for predicting the risk of developing a stroke, heart attack, or cardiovascular disease. Such a kit can include a lipocalin-2 binding component. In a preferred embodiment, the kit can include neutralizing antibodies or another lipocalin-2 antagonist. Kits can be used for risk assessment, diagnosis, and/or prognosis of stroke, heart attack, or cardiovascular disease.

In an embodiment, a kit can comprise a package including an assay for lipocalin-2 and instructions, and optionally related materials such as number or color charts, for correlating the level of lipocalin-2 as determined by the assay with a risk of developing a future cardiovascular disease or with other patient criteria as described above. In further embodiments, the kits also include an assay for cholesterol, CRP, MPO, or other CVD/CAD markers.

EXAMPLES

Example 1

Human Subjects 46 patients (mean age, 52±22 years; median age, 50 years; age range, 18 to 96 years; 48% female) were recruited to the study. Patients were classified as high-risk group in heart attack/stroke if they were (i) Coronary Artery Diseases: previous MI (>2 days prior to informed consent), or stable or previous unstable angina (>30 days prior to informed consent) with documented multivessel coronary artery disease or a positive stress test, or multivessel PTCA (>30 days prior to informed consent), or previous 15 multivessel CABG without angina (if surgery performed >4 years prior to informed consent) or with recurrent angina after surgery; (ii) Peripheral Arterial Disease: previous limb bypass surgery or angioplasty or amputation, intermittent claudication on history with ankle/arm BP ratio <0.8 on at least one side, or non-invasive testing; (iii) Previous stroke; (iv) TIA >7 days and <1 year prior to informed consent; (v) Diabetes Mellitus (types I or II): with evidence of end-organ damage (retinopathy, LVH, micro or macro albuminuria), or any evidence of previous cardiac or vascular disease.

A control group of 36 age and sex matched healthy subjects (mean age 65±18 years; median age, 72 years; age range, 23 to 87 years; 78% female) were included.

Figure 1B:
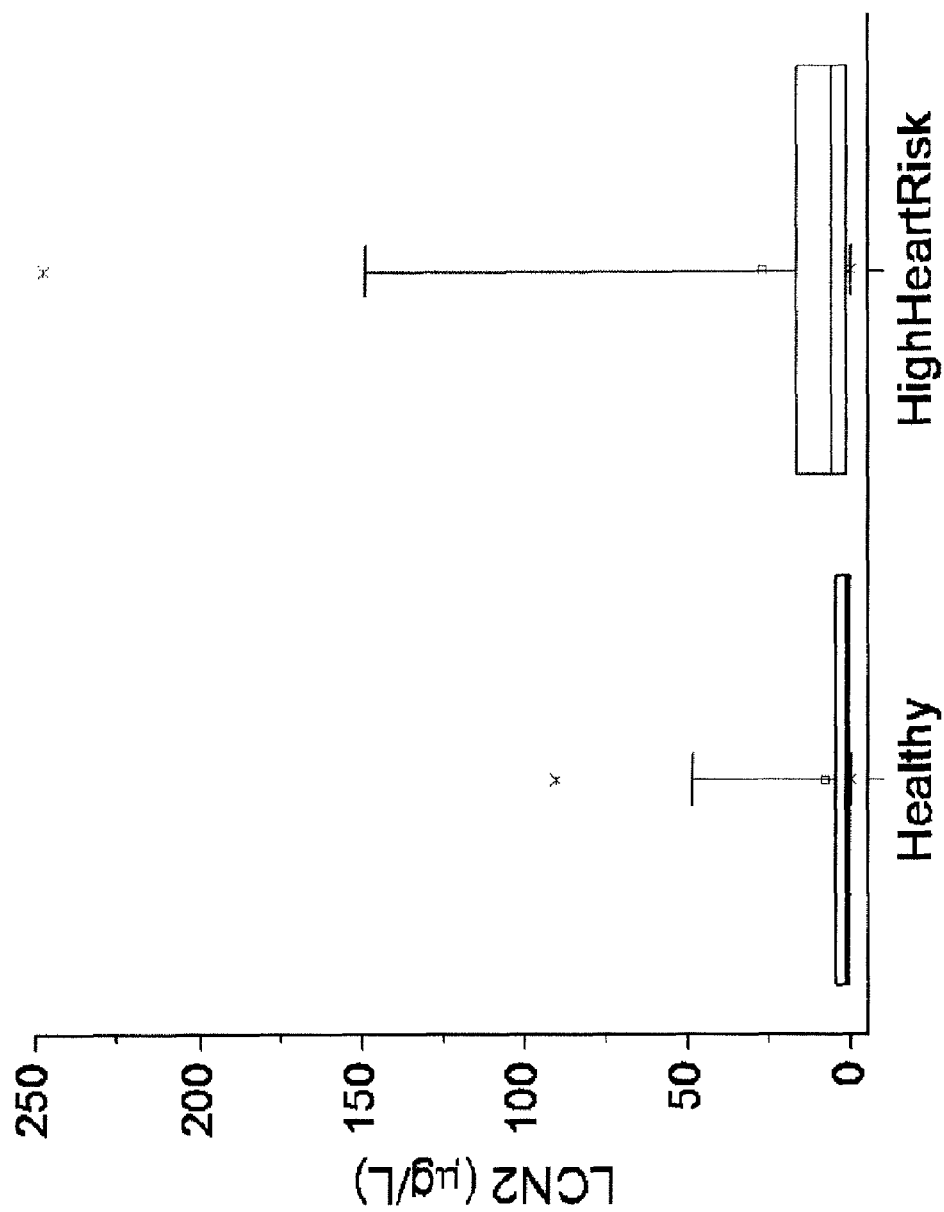

FIGS. 1A and 1B show the box plots of serum and urinary lipocalin-2 (LCN2) in patients with high-risk in heart attack/stroke and healthy controls. The median serum LCN2 concentration was significantly higher in patients with high-risk in heart attack/stroke than those in healthy subjects (51.6 vs 35.5 µg/L; P<0.001). The median urinary LCN2 concentration was also significantly higher in patients with high-risk in heart attack/stroke than those in healthy subjects (6.6 vs 1.6 µg/L; P<0.05).

Example 2

Antibody Production and Development of Sandwich ELISA for Quantification of Murine and Human Lipocalin-2

The polyclonal antibodies against the recombinant human or murine lipocalin 2 were generated in New Zealand female rabbits as described previously (17). Anti-human or murine lipocalin 2 IgG was purified from the immunized rabbit serum using protein A/G beads, followed by the affinity chromatography using their respective antigens as the ligands. The affinity-purified anti-human or anti-murine lipocalin 2 IgG was biotinylated with a kit from Pierce and used as the detection antibodies. The unlabeled anti-human or anti-murine lipocalin-2 IgG was used for coating a 96-well microtiter plate overnight at 4° C. Human or mouse serum was diluted (1:50) into PBS, and 100 µl of the diluted samples or recombinant standards were applied to each well and incubated at 37° C. for 1 h. The plates were washed three times and then incubated with 100 µl of the detection antibody for another 2 h. After washing for another three times with PBS, the wells were incubated with streptavidin-conjugated horseradish peroxidase for 1 h and subsequently reacted with tetramethylbenzidine reagent for 15 min. A total of 100 µl of 2 M $H_2SO_4$ was added to each well to stop the reaction, and the absorbance at 450 nm was measured. The intra- and inter-assay coefficients of variance were determined by measuring five serum samples in a total of six independent assays with duplicate determinations.

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference to the extent not inconsistent with the explicit teachings herein.

REFERENCES

1. Hraba-Renevey, S., Turler, H., Kress, M., Salomon, C., and Weil, R. 1989. SV40-induced expression of mouse gene 24p3 involves a post-transcriptional mechanism. *Oncogene.* 4:601-608.
2. Kjeldsen, L., Johnsen, A. H., Sengelov, H., and Borregaard, N. 1993. Isolation and primary structure of NGAL, a novel protein associated with human neutrophil gelatinase. *J Biol Chem.* 268:10425-10432.
3. Akerstrom, B., Flower, D. R., and Salier, J. P. 2000. Lipocalins: unity in diversity. *Biochim Biophys Acta.* 1482:1-8.
4. Flower, D. R. 1996. The lipocalin protein family: structure and function. *Biochem J.* 318:1-14.

5. Bratt, T., Ohlson, S., and Borregaard, N. 1999. Interactions between neutrophil gelatinase-associated lipocalin and natural lipophilic ligands. *Biochim Biophys Acta.* 1472:262-269.

6. Liu, Q., and Nilsen-Hamilton, M. 1995. Identification of a new acute phase protein. *J Biol Chem.* 270:22565-22570.

7. Kratchmarova, I., Kalume, D. E., Blagoev, B., Scherer, P. E., Podtelejnikov, A. V., Molina, H., Bickel, P. E., Andersen, J. S., Fernandez, M. M., Bunkenborg, J., et al. 2002. A proteomic approach for identification of secreted proteins during the differentiation of 3T3-L1 preadipocytes to adipocytes. *Mol Cell Proteomics.* 1:213-222.

8. Meheus, L. A., Fransen, L. M., Raymackers, J. G., Blockx, H. A., Van Beeumen, J. J., Van Bun, S. M., and Van de Voorde, A. 1993. Identification by microsequencing of lipopolysaccharide-induced proteins secreted by mouse macrophages. *J Immunol.* 151:1535-1547.

9. Jayaraman, A., Roberts, K. A., Yoon, J., Yarmush, D. M., Duan, X., Lee, K., and Yarmush, M. L. 2005. Identification of neutrophil gelatinase-associated lipocalin (NGAL) as a discriminatory marker of the hepatocyte-secreted protein response to IL-1beta: a proteomic analysis. *Biotechnol Bioeng.* 91:502-515.

10. Fujino, R. S., Tanaka, K., Morimatsu, M., Tamura, K., Kogo, H., and Hara, T. 2006. Spermatogonial Cell-mediated Activation of An I{kappa}B{zeta}-independent NF-{kappa}B Pathway in Sertoli Cells Induces Transcription of the Lipocalin-2 Gene. *Mol Endocrinol* 20:904-915.

11. Mishra, J., Dent, C., Tarabishi, R., Mitsnefes, M. M., Ma, Q., Kelly, C., Ruff, S. M., Zahedi, K., Shao, M., Bean, J., et al. 2005. Neutrophil gelatinase-associated lipocalin (NGAL) as a biomarker for acute renal injury after cardiac surgery. *Lancet.* 365:1231-1238.

12. Mishra J., Ma Q., Prada A., Mitsnefes M., Zahedi K., Yang J., Barasch J., Devarajan P., 2003. Identification of neutrophil gelatinase-associated lipocalin as a novel early urinary biomarker for ischemic renal injury. *Journal of the American Society of Nephrology.* 14(10):2534-43.

13. Mishra J., Mori K., Ma Q., Kelly C., Barasch J., Devarajan P., 2004. Neutrophil gelatinase-associated lipocalin: a novel early urinary biomarker for cisplatin nephrotoxicity. *American Journal of Nephrology.* 24(3):307-15.

14. Reghunathan R., Jayapal M., Hsu L. Y., Chng H. H., Tai D., Leung B. P., Melendez A. J., 2005. Expression profile of immune response genes in patients with Severe Acute Respiratory Syndrome. *BMC Immunology.* 6:2.

15. Hemdahl A. L., Gabrielsen A., Zhu C., Eriksson P., Hedin U., Kastrup J., Thoren P., Hansson G. K., 2006. Expression of neutrophil gelatinase-associated lipocalin in atherosclerosis and myocardial infarction. Arteriosclerosis, Thrombosis & Vascular Biology. 26(1):136-42.

16. Tschesche H., Zolzer V., Triebel S., Bartsch S., 2001. The human neutrophil lipocalin supports the allosteric activation of matrix metalloproteinases. *European Journal of Biochemistry.* 268(7):1918-28.

17. Xu, A., Lam, M. C., Chan, K. W., Wang, Y., Zhang, J., Hoo, R. L., Xu, J. Y., Chen, B., Chow, W. S., Tso, A. W., et al. 2005. Angiopoietin-like protein 4 decreases blood glucose and improves glucose tolerance but induces hyperlipidemia and hepatic steatosis in mice. *Proc Natl Acad Sci USA* 102:6086-6091.

We claim:

1. A method for characterizing a subject's risk of cardiovascular disease, comprising:
    obtaining a body fluid sample from a subject that exhibits neither symptoms of heart failure nor symptoms of renal dysfunction,
    measuring the level of lipocalin-2 in the sample, comparing the subject's lipocalin-2 level to a predetermined reference value, and
    characterizing the subject's risk of cardiovascular disease, wherein the predetermined reference value is determined based on lipocalin-2 levels in a population, and wherein an elevated lipocalin-2 level in the sample compared to the predetermined reference value is predictive of increased risk, and
    wherein the subject's lipocalin-2 level being no greater than the lowest 25% of the lipocalin-2 levels forming the population indicates that the subject has a low risk of cardiovascular disease, the subject's lipocalin-2 level ranging from the lowest 25%-50% of the lipocalin-2 levels forming the population indicates that the subject has a low intermediate risk of cardiovascular disease, the subject's lipocalin-2 level ranging from the 50%—the highest 75% of the lipocalin-2 levels forming the population indicates that the subject has an intermediate risk of cardiovascular disease, and the subject's lipocalin-2 level greater than the highest 75% of the lipocalin-2 levels forming the population indicates that the subject has a high risk of cardiovascular disease.

2. The method according to claim 1, wherein the predetermined value is a single value, multiple values, a single range, or multiple ranges.

3. The method according to claim 2, wherein the predetermined value is a plurality of predetermined marker level ranges, wherein the comparing of the subject's lipocalin-2 level to the predetermined reference value comprises:
    determining in which of the predetermined marker level ranges the subject's lipocalin-2 level falls.

4. The method according to claim 1, wherein the cardiovascular disease is chronic heart disease, acute coronary syndrome, myocardial infarction, atherosclerosis, microvascular disease, or stroke.

5. The method according to claim 1, further comprising:
    measuring the level of a second marker of cardiovascular disease or inflammation in the sample and correlating the level of lipocalin-2 with the level of the second marker, wherein the combination of lipocalin-2 level and second marker level is predictive of risk.

6. The method according to claim 5, wherein the second marker is selected from the group consisting of a cholesterol fraction, C-reactive protein (CRP), and myeloperoxidase (MPO); and further comprising establishing a first risk value based on the lipocalin-2 level, comparing the level of cholesterol, CRP, or MPO with a second predetermined reference value to establish a second risk value, and
    characterizing the subject's risk based on a combination of the first and second risk values.

7. The method according to claim 6, wherein the combination of first and second risk values establishes a third risk value different from the first and second risk values.

8. The method according to claim 1, wherein the measurement is taken repeatedly over time to monitor the change of cardiovascular disease risk over time.

9. The method according to claim 1, wherein the body fluid sample is blood, serum, plasma, urine, saliva, or tears.

10. The method according to claim 1, further comprising communicating the subject's risk of developing cardiovascular disease or administering a treatment regimen to reduce said risk.

11. The method according to claim 1, wherein the cardiovascular disease is chronic heart disease.

12. The method according to claim 1, wherein the cardiovascular disease is acute coronary syndrome.

13. The method according to claim 1, wherein the cardiovascular disease is myocardial infarction.

14. The method according to claim 1, wherein the cardiovascular disease is atherosclerosis.

15. The method according to claim 1, wherein the cardiovascular disease is microvascular disease.

16. The method according to claim 1, wherein the cardiovascular disease is stroke.

* * * * *

UNITED STATES PATENT AND TRADEMARK OFFICE
CERTIFICATE OF CORRECTION

PATENT NO. : 8,030,097 B2  
APPLICATION NO. : 12/113056  
DATED : October 4, 2011  
INVENTOR(S) : Aimin Xu et al.

Page 1 of 1

It is certified that error appears in the above-identified patent and that said Letters Patent is hereby corrected as shown below:

Column 1,  
Lines 60-61, "metallopeptidase 9 suggests" should read --metallopeptidase 9 (MMCN9) suggests--.  
Lines 61-62, "modulatory actions on MMP9 by" should read --modulatory actions on MMCN9 by--.  
Line 62, "by protecting MMP9 from" should read --by protecting MMCN9 from--.  
Line 64, "demonstrated MMP9 and" should read --demonstrated MMCN9 and--.  
Line 67, "MMP9 activity" should read --MMCN9 activity--.

Column 2,  
Line 1, "modulating MMP9" should read --modulating MMCN9--.

Column 4,  
Lines 21-22, "Examples of such markers are include interleukin-1" should  
read --Examples of such markers include interleukin-1--.

Column 9,  
Line 30, "PF-cyanin-5" should read --PE-cyanin-5--.  
Lines 34-35, "PE-Texas Red (FCD)" should read --PE-Texas Red (ECD)--.  
Line 37, "and PE-Cy7," should read --and PE+PE-Cy7,--.

Column 10,  
Lines 37-38, "A method of evaluating the likelihood that an individual that to be treated"  
should read --A method of evaluating the likelihood that an individual that is to be treated--.

Signed and Sealed this  
Twentieth Day of March, 2012

David J. Kappos  
*Director of the United States Patent and Trademark Office*